US00PP21454P2

(12) United States Plant Patent
Pieters

(10) Patent No.: US PP21,454 P2
(45) Date of Patent: Nov. 9, 2010

(54) ***CHRYSANTHEMUM* PLANT NAMED 'PPP ALUG 09'**

(50) Latin Name: *Chrysanthemum morifolium*
Varietal Denomination: PPP ALUG 09

(75) Inventor: Dirk Pieters, Oostnieuwkerke (BE)

(73) Assignee: Paraty BVBA, Oostniewkerke (BE)

( * ) Notice: Subject to any disclaimer, the term of this patent is extended or adjusted under 35 U.S.C. 154(b) by 0 days.

(21) Appl. No.: 12/462,577

(22) Filed: Aug. 5, 2009

(51) Int. Cl.
*A01H 5/00* (2006.01)

(52) U.S. Cl. ..... Plt./288
(58) Field of Classification Search ..... Plt./288, Plt./287
See application file for complete search history.

*Primary Examiner*—Annette H Para
*Assistant Examiner*—Louanne C Krawczewicz Myers
(74) *Attorney, Agent, or Firm*—Mark P. Bourgeois

(57) ABSTRACT

A new and distinct *Chrysanthemum* plant cultivar is disclosed, characterized by large decorative type inflorescences with white ray florets and a creamy yellow center, consistent flowering response to short days, blooming consistently after 49 days of short day length, free branching habit, and a consistent natural season flowering habit during the third week of September.

1 Drawing Sheet

Latin name of the genus and species *Chrysanthemum morifolium.*

Variety denomination: 'PPP ALUG 09'.

BACKGROUND OF THE INVENTION

The new cultivar 'PPP ALUG 09' is a product of a cross between the male parent 'PPP ALB WH06' (U.S. Plant Pat. No. 19,268) and the female parent 'Dark Veria' (U.S Plant Pat. No. 10,215). The new cultivar was discovered and selected by Dirk Pieters in September of 2008 in a greenhouse in Oostnieuwkerke, Belgium.

Asexual reproduction of the new cultivar 'PPP ALUG 09' by terminal cuttings was performed in Oostnieuwkerke, Belgium and Oxnard, Calif., and has shown that the unique features of this new cultivar are stable and reproduced true to type on successive generations.

SUMMARY OF THE INVENTION

The cultivar 'PPP ALUG 09' has not been observed under all possible environmental conditions. The phenotype may vary somewhat with variations in environment such as temperature, daylength, and light intensity, without, however, any variance in genotype. The following traits have been repeatedly observed and are determined to be the unique characteristics of 'PPP ALUG 09.' These characteristics in combination distinguish 'PPP ALUG 09' as a new and distinct *Chrysanthemum* cultivar:

1. Large, white, decorative-type inflorescences with a pale yellow center;
2. Consistent natural season flowering habit during the third week of September;
3. Free branching habit; and
4. Consistent flowering response to short days, blooming consistently after 49 days of short day length.

Plants of the new cultivar 'PPP ALUG 09' are similar to plants of the male parent variety, 'PPP ALB WH06' in most horticultural characteristics; however plants of the new cultivar 'PPP ALUG 09' are smaller in both height and plant spread. Additionally, the male parent has longer inflorescence longevity. Finally, the inflorescences of 'PPP ALUG 09' have a pale yellow center compared to the creamy white center of the male parent.

Plants of the new cultivar 'PPP ALUG 09' are similar to plants of the female parent variety, 'Dark Veria' in most horticultural characteristics, however plants of the new cultivar 'PPP ALUG 09' are taller and wider in both height and plant spread. Also, the female parent has a wider inflorescence diameter and more inflorescences per lateral branch. Additionally, the ray florets of 'PPP ALUG 09' are white compared to the yellow ray florets of the female parent. Finally, 'PPP ALUG 09' naturally blooms three weeks earlier than the female parent.

In comparison to the commercially available variety 'GEDI THREE MIL' (U.S. Plant Pat. No. 16,843), 'PPP ALUG 09' is smaller in both height and plant spread. Additionally, the new variety 'PPP ALUG 09' has a smaller inflorescence diameter and brighter white ray florets. Finally, the comparable variety 'GEM THREE MIL' has more inflorescences per lateral branch.

BRIEF DESCRIPTION OF THE PHOTOGRAPH

The accompanying photograph in the drawing illustrates in full color a typical plant of 'PPP ALUG 09' grown in a 2 gallon container. One cutting was used in the pot, planted mid May and grown under outdoor field conditions. The colors are as nearly true as is reasonably possible in a color representation of this type.

DETAILED BOTANICAL DESCRIPTION

In the following description, color references are made to The Royal Horticultural Society Colour Chart except where general terms of ordinary dictionary significance are used. The following observations and measurements describe 'PPP ALUG 09' plants grown in Oxnard, Ventura County, Calif., during the months of May through October 2006.

The growing temperature ranged from 12° C. to 15° C. at night to 12° C. to 20° C. during the day. Measurements and numerical values represent averages of typical flowering types.

Botanical classification: *Chrysanthemum morifolium* 'PPP ALUG 09'.

Commercial classification: Garden-type *Chrysanthemum.*

PROPAGATION

Time to rooting: 7 to 14 days at approximately 21° C.

Root description: Fine, fibrous.

PLANT

Growth habit: Mounding herbaceous perennial.

Height: Approximately 18 cm.

Plant spread: Approximately 30 cm.

Growth rate: Moderate.

Branching characteristics: Free branching.

Length of lateral branches: Approximately 14 cm.

Diameter of lateral branches: About 4.6 mm.

Color of lateral branches: Near Yellow Green 147B.

Number of leaves per lateral branch: Approximately 22.

Age of plant described: Approximately 138 days.

FOLIAGE

Leaf:

*Arrangement.*—Alternate single.

*Average length.*—Approximately 5.1 cm.

*Average width.*—Approximately 4.6 cm.

*Shape of blade.*—Ovate.

*Apex.*—Acuminate.

*Base.*—Attenuate.

*Attachment.*—Stalked.

*Margin.*—Serrate.

*Disc diameter.*—Approximately 1.1 cm.

*Receptacle height.*—About 5 mm.

*Receptacle diameter.*—About 4 mm.

*Fragrance.*—None.

*Texture of top surface.*—Lightly pubescent.

*Texture of bottom surface.*—Lightly pubescent.

*Leaf internode length.*—Approximately 0.6 cm.

*Color.*—Young foliage upper side: Near Yellow-Green 147A. Young foliage under side: Near Yellow-Green 147B. Mature foliage upper side: Near Yellow-Green 147A. Mature foliage under side: Near Yellow-Green 147B.

*Venation.*—Type: Palmately net. Venation color upper side: Near Green 138B. Venation color under side: Near Green 138B.

Petiole:

*Average length.*—Approximately 1.3 cm.

*Color.*—Near Green 138A.

*Diameter.*—Approximately 0.3 cm.

BLOOM

Inflorescence:

*Flowering habit.*—Induced by darkness period greater than 13.5 hours, approximately 49 days of appropriate day length required to induce and develop blooms.

*Inflorescence form.*—Decorative.

*Natural flowering season.*—Approximately the third week in September.

*Number of inflorescences per lateral branch.*—Approximately 14.

*Inflorescence diameter.*—Approximately 5.3 cm.

*Inflorescence depth.*—Approximately 1.2 cm.

*Inflorescence longevity on plant.*—Approximately 26 to 30 days.

*Persistence.*—Persistent.

Ray florets:

*Appearance.*—Matte.

*Texture (both surfaces).*—Smooth.

*Average number of ray florets per inflorescence.*—200.

*Shape.*—Oblanceolate.

*Aspect.*—Flat.

*Margin.*—Entire.

*Apex.*—Obtuse.

*Base.*—Attenuate.

*Length.*—Approximately 1.5 cm.

*Width.*—Approximately 0.4 cm.

*Color.*—Upper surface at first opening: Near Yellow-White 158A. Upper surface at maturity: Near White 155B. Upper surface at fading: Near White 155D. Under surface at first opening: Near Yellow-White 158A. Under surface at maturity: Near White 155B. Under surface at fading: Near White 155D.

Disc florets:

*Appearance.*—Shiny.

*Texture.*—Smooth.

*Average number of florets per disc.*—Approximately 30.

*Shape.*—Cylindric.

*Apex.*—Obtuse.

*Average length.*—Approximately 0.3 cm.

*Average width.*—Approximately 0.1 cm.

*Color.*—At first opening: Near Yellow-Green 154D. At maturity: Near Yellow 10C. At fading: Near Yellow 10D.

Peduncle:

*Length.*—At terminal end (shortest): Approximately 3.3 cm. At lateral end (longest): Approximately 6.4 cm.

*Angle to stem.*—Acute.

*Strength.*—Moderate.

*Color.*—Near Green 138A.

*Habit.*—Upright.

*Diameter.*—Approximately 0.2 cm.

*Surface texture.*—Lightly pubescent.

Inflorescence bud:

*Length.*—Approximately 0.5 cm.

*Diameter.*—Approximately 0.5 cm.

*Form.*—Globular.

*Color.*—Near Yellow-White 158A.

Involucral bracts (phyllaries):

*Appearance.*—Matte.

*Texture.*—Lightly pubescent.

*Number.*—Approximately 23.

*Shape.*—Lanceolate.

*Margin.*—Entire.

*Apex.*—Obtuse.

*Length.*—Approximately 0.4 cm.

*Width.*—Approximately 0.2 cm.

*Color.*—Upper side: Near Green 137B. Under side: Near Green 137C.

REPRODUCTIVE ORGANS

Ray florets: Number of pistils per floret: 1. Stigma shape: 2 branched. Stigma color: Near Yellow 9C. Style color: Near Green-Yellow 1C. Style length: Approximately 0.2 cm. Stamens: Absent.

Disc florets: Number of pistils per floret: 1. Stigma shape: Cylindric. Stigma color: Near Yellow 9A. Style length: Approximately 0.2 cm. Style color: Near Green-Yellow 1C. Number of stamens per floret: Approximately 5. Anther shape: Tubular. Anther color: Near Yellow 9C. Pollen color: No pollen detected.

OTHER CHARACTERISTICS

Disease resistance: Neither resistance nor susceptibility to diseases or pests has been observed in this variety.

Drought tolerance/cold tolerance: Flowering plants are hardy to low temperatures about −2° C. Non-flowering plants are hardy in the approximate range of 3° C. to −6° C., depending upon duration of cold and amount of moisture in the soil. With adequate water plants are hardy to a high temperature of 45° C.

Fruit/seed production: Commercially, this plant is not used or observed in a stage where seeds would be produced. Therefore, seed production has not been observed.

What is claimed is:

1. A new and distinct cultivar of *Chrysanthemum* plant named 'PPP ALUG 09' as herein illustrated and described.

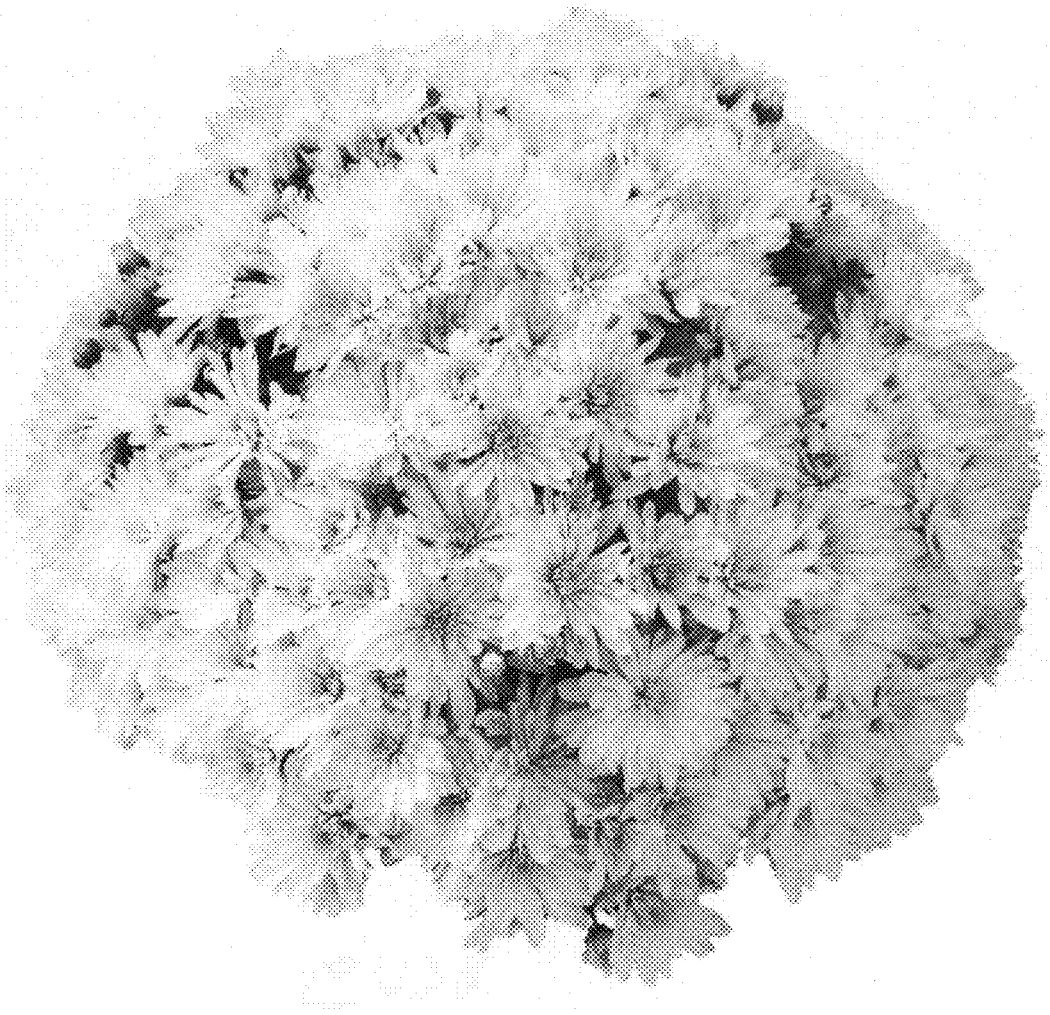

* * * * *